United States Patent [19]

Austermühle-Bertola

[11] 4,174,347

[45] Nov. 13, 1979

[54] PREPARATION OF ESTERS

[75] Inventor: Helena Austermühle-Bertola, Amsterdam, Netherlands

[73] Assignee: Shell Internationale Research Maatschappij B.V., Netherlands

[21] Appl. No.: 916,590

[22] Filed: Jun. 19, 1978

[51] Int. Cl.$^2$ .................. C07C 120/00; C07C 121/00
[52] U.S. Cl. ................................. 260/465.4; 260/464; 260/465 D
[58] Field of Search ............................ 260/464, 465.4

[56] References Cited

U.S. PATENT DOCUMENTS 3,992,432  11/1976  Napier et al. ...................... 260/465.1

OTHER PUBLICATIONS

Bernthsen, A Textbook of Org. Chem., (1931), p. 182, Van Nostrand, N.Y.
Royals, Adv. Org. Chem., (1954), pp. 604–605, Constable and Co., London.
C. A., 1972–1976 Chem. Sub. Index., 9th Coll., p. 473cs.
C. A., Trofimov et al., 80 (1974) 70356w.
C. A., Ilford Ltd., 82 (1975) 132125x.

*Primary Examiner*—Joseph Paul Brust
*Attorney, Agent, or Firm*—Pravel, Gambrell, Hewitt, Kirk, Kimball & Dodge

[57] ABSTRACT

A process for the preparation of an ester of cyanoacetic acid having the following general formula:

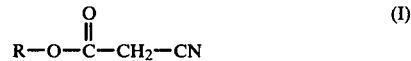

(wherein R represents an aliphatic or cycloaliphatic hydrocarbyl group), which comprises contacting an alkali metal carboxylate of general formula:

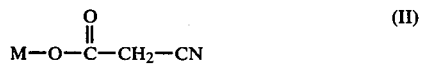

(wherein M represents an alkali metal atom) with a hydrocarbyl halide of general formula:

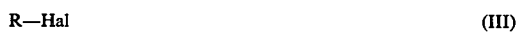

(wherein R has the meaning hereinbefore defined and Hal is a halogen atom having an atomic number of at least 17) in the presence of a phase transfer catalyst and an organic solvent.

8 Claims, No Drawings the halides of the general formular III may be primary, secondary or tertiary. The carbon-carbon bonds in the aliphatic or cycloaliphatic hydrocarbyl group R may all be saturated or one or more of them may be unsaturated. The process according to the present invention is of particular importance when R in the general formula III represents a group of the general formula:

PREPARATION OF ESTERS

BACKGROUND OF THE INVENTION

This invention relates to a process for the preparation of an ester of cyanoacetic acid which is a valuable chemical intermediate, especially in the preparation of pesticides such as esters of 2-(2,2-dichlorovinyl)-cyclopropanecarboxylic acids, such as are disclosed in U.K. Pat. No. 1,413,491.

In a preferred embodiment of this invention 3-methyl-2-butenyl cyanoacetate, sometimes known as prenyl cyanoacetate (PCA):

$$\begin{array}{c}CH_3\\ \phantom{C}\diagdown\\ \phantom{CH_3}C=C\\ \diagup\phantom{C}\diagdown\\ CH_3\phantom{C=C}H\end{array}\begin{array}{c}CH_2-O\\ \phantom{C}\diagdown\\ \phantom{CH_2CN}C=O\\ \diagup\\ CH_2CN\end{array}\quad(PCA)$$

is produced. PCA is a valuable intermediate in the manufacture of ethyl 3,3-dimethyl-2-(2,2-dichlorovinyl)-cyclopropanecarboxylate (EDV) which is itself the acid half of the well-known synthetic insecticidally-active pyrethoid ester "cypermethrin" (alpha-cyano-3-phenoxybenzyl 3,3-dimethyl-2-(2,2-dichlorovinyl) cyclopropanecarboxylate as disclosed in U.K. Pat. No. 1,413,491.

PCA can be converted into EDV by means of the following steps:

(a) PCA is rearranged by reaction with sodium hydroxide, in accordance with the procedure of Belgium Pat. No. 847,534, to produce 2-cyano-3,3-dimethylpent-4-enoic acid (CDPA):

$$\begin{array}{c}\phantom{HOOC-CH-}CH_3\\ \phantom{HOOC-CH-}|\\ HOOC-CH-C-CH=CH_2;\\ |\phantom{HOOC-}|\\ CN\phantom{HO}CH_3\end{array}$$

(b) CDPA is reacted with carbon tetrachloride, according to the procedure of Belgium Pat. No. 856,490, to produce 2-cyano-3,3-dimethyl-4,6,6,6 tetrachlorohexanoic acid (CDTA):

$$\begin{array}{c}\phantom{HOOC-CH-}CH_3\phantom{-}Cl\\ \phantom{HOOC-CH-}|\phantom{-CH-}|\\ HOOC-CH-C\phantom{-}\phantom{-}CH-CH_2-CCl_3;\\ |\phantom{HOOC-}|\\ CN\phantom{HO}CH_3\end{array}$$

(c) CDTA is cyclized, dehydrohalogenated and decarboxylated in the presence of a base, according to the procedure of Belgium Pat. No. 855,691, to produce 3,3-dimethyl-2-(2,2-dichlorovinyl) cyclopropanenitrile (DCVN):

$$\begin{array}{c}H\phantom{-----}CH=CCl_2\\ \diagdown\phantom{--}\diagup\\ \phantom{-----}C\\ \diagup\phantom{-}\diagdown\\ CH_3-C\phantom{------}C-H;\text{ and}\\ \diagup\phantom{-------}\diagdown\\ CH_3\phantom{---------}CN\end{array}$$

(d) DCVN is hydrolyzed in the presence of dilute mineral acid in ethanol to produce EDV.

Although PCA, as produced by the process of this invention, is a compound of particular importance, other cyanoacetic acid esters within the scope of this invention process similar utility as intermediates in the production of insecticically-active compounds.

SUMMARY OF THE INVENTION

The present invention provides a process for the preparation of an ester of cyanoacetic acid having the following general formula:

$$R-O-\underset{\underset{\displaystyle\|}{O}}{C}-CH_2-CN \qquad (I)$$

wherein R represents an aliphatic or cycloaliphatic hydrocarbyl group, which comprises mixing and reacting an alkali metal carboxylate of general formula:

$$M-O-\underset{\underset{\displaystyle\|}{O}}{C}-CH_2-CN \qquad (II)$$

wherein M represents an alakli metal atom, with a hydrocarbyl halide of general formula:

$$R-Hal \qquad (III)$$

wherein R has the meaning hereinbefore defined and Hal is a halogen atom having an atomic number of at least 17, in the presence of a phase transfer catalyst and an organic solvent for the hydrocarbyl halide.

In the reaction of an alkali metal carboxylate of the general formula II with a halide of the general formula III in the presence of a phase transfer catalyst, an undesirable side-reaction may take place with the formation of compounds of the general formula:

$$R-O-\underset{\underset{\displaystyle\|}{O}}{C}-\underset{\underset{\displaystyle|}{R}}{CH}-CN \qquad (IV)$$

wherein R has the same meaning as in the general formula I; the latter reaction tends to occur at temperatures above 100° C. and is clearly undesirable because it decreases the yield of the desired compounds of the general formula I. An attractive feature of the process according to the invention is that it allows the use of a relatively low reaction temperature, for example between 20° and 100° C., and thereby avoids the production of substantial quantities of unwanted by-products; a low yield of by-product IV is particularly noticeable when the organic solvent is a halogenated hydrocarbon normally liquid at ambient temperatures, especially a chlorinated hydrocarbon of one to four carbon atoms, e.g. carbon tetrachloride, chloroform, dichloromethane and perchloroethylene, or an aromatic hydrocarbon, normally liquid at ambient temperatures, especially an alkylbenzene, e.g. toluene or a xylene or mixture of xylenes. Carbon tetrachloride and xylene have shown excellent properties in this respect.

The halides of the general formular III may be primary, secondary or tertiary. The carbon-carbon bonds in the aliphatic or cycloaliphatic hydrocarbyl group R may all be saturated or one or more of them may be unsaturated. The process according to the present invention is of particular importance when R in the general formula III represents a group of the general formula:

wherein $R^1$, $R^2$, $R^3$, $R^4$ and $R^5$ each independently represent a hydrogen atom or a hydrocarbyl group, for example an alkyl of one to four carbon atoms, a cycloalkyl or an aryl group or a combination of any of these atoms and groups, because intermediates for the preparation of particularly valuable pesticides are obtained. Moreover, halides of the general formula III wherein R represents a group of the general formula V are generally stable and do not decompose at a temperature below 100° C. Preferably $R^2$, $R^3$ and $R^4$ in the general formula V each represent a hydrogen atom or a methyl group and $R^1$ and $R^5$ represent hydrogen atoms. The preferred starting compound of the general formula III is 1-chloro-3-methyl-2-butene.

In the alkali metal carboxylate of general formula II the alkali metal atom M may be lithium, sodium, potassium, rubidium or cesium but, for economic reasons, sodium or potassium are generally preferred. Very good results have been obtained with potassium cyanoacetate.

The phase transfer catalyst may be any reagent which is capable of accelerating interphase reactions taking place in two-Phase systems and may take the form of an onium salt, a macrocyclic polyether, or a surface-active agent.

The phase transfer catalyst may be: an onium salt, particularly a quaternary onium salt of the general formula:

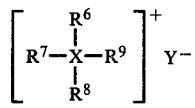

wherein X represents a nitrogen, phosphorus or arsenic atom, $R^6$, $R^7$, $R^8$ and $R^9$ each an alkyl, aralkyl, alkaryl or aryl group and Y a monovalent ion, e.g. halide such a chloride, bromide or iodide, or an alkylsulphate such as methylsulphate or ethylsulphate; or a sulphonium salt of the general formula:

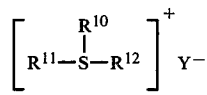

wherein $R^{10}$, $R^{11}$ and $R^{12}$ each represent an alkyl group and Y a monovalent ion, e.g. a halide such as chloride, bromide or iodide, or an alkylsulphate such as methylsulphate or ethylsulphate. Preferably, with respect to the groups $R^6$ through $R^{12}$, the alkyl groups contain 1 to 18 carbon atoms and the aralkyl and alkaryl groups contain up to 10 carbon atoms; the aryl group is preferably phenyl.

Examples of suitable onium salts are tetra-n-butylammonium bromide, tetra-n-butylammonium chloride, methyltrioctylammonium chloride, methyltri-(2-methylheptyl)ammonium chloride, methyltri-2-methylphenyl-ammonium chloride, tetramethyl-phosphonium iodide, tetra-n-butylphosphonium bromide, ethyl-2-methylpentyl-2-methylundeclysulphonium ethylsulphate, methyltriphenylarsonium iodide, ethyl-2-methylpentadecyl-2-methyl-undecyl-sulphonium ethylsulphate, methyldinonyl-sulphonium methylsulphate and n-hexadecyldimethylsulphonium iodide. Very good results have been obtained with quaternary ammonium compounds.

The onium salt may be a hydroxide or a salt and can be employed as the functional portion of a strongly-basic anion exchange resin having a structural portion (polymer matrix) and a functional portion (ion-active group). Of special importance are polystyrene resins, such a copolymers of aromatic monovinyl compounds and aromatic polyvinyl compounds, particularly styrene/divinylbenzene copolymers. The functional portion is a quaternary ammonium, phosphonium or arsonium group. Examples of strongly-based anion exchange resins which may be employed are those derived from trimethylamine (such as the products known under the trade names of "Amberlite IRA-400", "Amberlite IRA-401", Amberlite IRA-402", "Amberlite IRA-900", "Duolite A-101-D", "Duolite ES-111", "Dowex 1", "Dowex 11", "Dowex 21K", and "Ionac A-450"), and those derived from dimethylethanol amine (such as the products known under the trade names of "Amberlite IRA-410", "Amberlite IRA-911", "Dowex 2", "Duolite A-102-D", "Ionac A-542" and "Ionac A-550"). Very good results have been obtained with those derived from trimethylamine.

Other suitable phase transfer catalysts are macrocyclic polyethers known as "crown ethers". These compounds, together with their preparation, are described in the literature, for example in Tetrahedron Letters No. 18(1972) pages 1793–1796, and are commonly designated by reference to the total number of atoms forming the macrocyclic ring together with the number of oxygen atoms in that ring. Thus the macrocyclic polyether whose formal chemical name is 1,4,7,10,13,16-hexaoxacyclooctadecane is designated as "18-crown-6". Other examples of suitable macrocyclic polyethers are 3,4,-benzo-1,6,9,12,15,18,21-macrocyclic polyethers are 3,4-benzo-1,6,9,12,15,18,21-heptaoxacyclotricos-3-ene and 3,4-benzo-1,6,9,12-tetraoxacyclotetradec-3-ene. 18-Crown-6 is particularly suitable.

Other suitable phase transfer catalysts are surface-active agents. A "surface-active agent" is defined as in Kirk-Othmer, "Encyclopedia of Chemical Technology", second edition, volume 19(1969) page 508: "An organic compound that encompasses in the same molecule two dissimilar structural groups, one being water-soluble and one being water-insoluble".

The surface-active agent is preferably non-ionic, such as a poly-(alkyleneoxy) derivative formed by reacting a higher alcohol, alkylphenol or fatty acid with ethylene oxide or propylene oxide. Suitable alcohols, alkylphenols or fatty acids contain an alkyl group of 8–20 carbon atoms and the number of alkyleneoxy units is in the range of 1–50. A particularly suitable non-ionic surface-active agent (referred to in the examples as "Dobanol 91-6") is formed from a $C_6$-$C_{11}$ n-alkanol mixture and contains an average of six ethyleneoxy units. The non-ionic surface-active agent may be an alkylbenzene containing a straight alkyl group. Suitable alkylbenzenes contain an alkyl group of 8–20 carbon atoms.

The molar ratio of the phase transfer catalyst to the halide of the general formula III can vary within wide limits, but is suitably from 1:5 to 1:5,000 and preferably from 1:20 to 1:200. The molar ratio of the alkali metal carboxylate of the general formula II to the halide of the general formula III can also vary within wide limits, but is suitably from 1:0.75 to 1:1, the equimolar ratio being preferred.

The process may suitably be carried out by stirring the starting compounds, the onium salt and the organic solvent for periods of up to five hours at temperatures preferably from 20° to 100° C. Longer times can be used but are unnecessary to improve yield.

The compound of the general formula I may be isolated from the reaction mixture by washing it with water to remove the simultaneously formed alkali metal halide, drying the washed mixture and fractionating the dried mixture.

Compounds generated by the process according to the invention and having the following general formula are novel compounds and, accordingly represent another feature of the present invention:

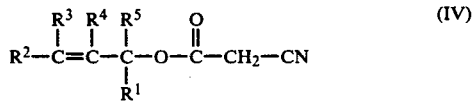
(IV)

wherein each of $R^1$, $R^2$, $R^3$, $R^4$ and $R^5$ independently represent a hydrogen atom or a hydrocarbyl group, e.g. an alkyl group of one to four carbon atoms such as a methyl group. An example of such a novel compound is 3-methyl-2-butenyl cyanoacetate.

The following examples illustrate the process according to the invention and the novel compounds produced therefrom.

EXAMPLES I TO VI

A vessel was charged with 25 mmol of potassium cyanoacetate, 25 mmo. of 1-chloro-3-methyl-2-butene, tetra-n-butylammonium chloride and 25 ml of a solvent. The contents of the vessel were stirred for a certain period. The mixture formed was washed twice with 10 ml of water, the washed mixture was dried in the presence of anhydrous magnesium sulphate, the magnesium sulphate was removed by filtration and the filtrate was boiled down. Analysis by means of gas-liquid chromatography showed that the residue consisted of 3-methyl-2-butenyl cyanoacetate (x mmole) and 3-methyl-2-butenyl 2-cyano-5-methyl-4-hexenoate, expressed in %, were calculated as $$\frac{x}{x+2y} \times 100 \text{ and } \frac{2y}{x+2y} \times 100,$$

respectively. The yield of 3-methyl-2-butenyl cyanoacetate, expressed in %, was calculated as
(conversion of 1-chloro-3-methyl-2-butene x selectivity to 3-methyl-2-butenyl cyanoacetate)/100

Six experiments were conducted in the manner described above. The table shows the solvents used, the amounts of tetra-n-butyl-ammonium chloride employed, calculated on 1-chloro-3-methyl-2-butene, the temperatures, the reaction times and the results.

TABLE

| Example No. | Solvent | Tetra-n-butyl-ammonium chloride, % mole | Temperature, °C | Reaction time, h | Conversion of 1-chloro-3-methyl-2-butene, % | Selectivity, %, to 3-methyl-2-butenyl | | Yield, %, of 3-methyl-2-butenyl cyanoacetate |
|---|---|---|---|---|---|---|---|---|
| | | | | | | cyanoacetate | 2-cyano-5-methyl-4-hexenoate | |
| I | CCl₄ | 2 | 90 | 4 | 92 | 98 | 2 | 90 |
| II | CHCl₃ | 5 | 77 | 4 | 92 | 86 | 14 | 79 |
| III | CH₂Cl₂ | 20 | 36 | 2 | 95 | 82 | 18 | 78 |
| IV | xylene *) | 2 | 70 | 7 | 78 | 95 | 5 | 74 |
| V | " | 1 | 110 | 1½ | 90 | 62 | 38 | 56 |
| VI | " | 20 | 115 | 1 | 99 | 53 | 47 | 53 |

*) a mixture of o-, m- and p-xylene

From the foregoing, those of ordinary skill in the art may make modifications and variation of the practice of the invention without departing from the scope of the invention as claimed herein.

I claim:

1. A process for the preparation of an ester of cyanoacetic acid having the following general formula:

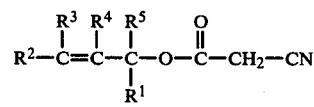

wherein $R^1$, $R^2$, $R^3$, $R^4$ and $R^5$ each independently represent a hydrogen atom, an alkyl group of one to four carbon atoms, or a cycloalkyl group, which comprises mixing and reacting an alkali metal carboxylate of general formula:

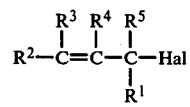
(II)

wherein M represents an alkali metal atom, with a hydrocarbyl halide of general formula:

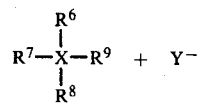

wherein $R^1$, $R^2$, $R^3$, $R^4$ and $R^5$ are as defined above and Hal is a halogen atom having an atomic number of at least 17, in the presence of a phase transfer catalyst selected from the group consisting of a quaternary onium salt of the general formula

wherein X represents a nitrogen, phosphorus or arsenic atom, $R^6$, $R^7$, $R^8$ and $R^9$ represent, independently, an alkyl group containing 1 to 18 carbon atoms or an aralkyl or aryl group containing up to 10 carbon atoms, and Y represents a monovalent ion; a ternary sulphonium salt of the general formula

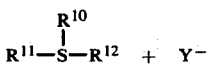

wherein $R^{10}$, $R^{11}$ and $R^{12}$ each, independently, represents an alkyl group containing 1 to 18 carbon atoms and Y represents a monovalent ion; a macrocyclic polyether selected from the group consisting of 1,4,7,10,13,16-hexaoxacyclooctadecane, 3,4-benzo-1,6,9,12,15,18,21-heptaoxacyclotricos-3-ene and 3,4-benzo-1,6,9,12-tetraoxycyclotetradec-3,-ene; and in the presence of an organic solvent for the hydrocarbyl halide, at a temperature in the range of from about 20° C. to about 100° C.

2. A process according to claim 1 wherein the phase transfer catalyst is a quaternary ammonium salt.

3. A process according to claim 1 wherein the phase transfer catalyst is tetra-n-butyl-ammonium chloride.

4. A process according to claim 1 wherein the organic solvent is a halogenated hydrocarbon or an aromatic hydrocarbon.

5. A process according to claim 7 wherein the chlorinated hydrocarbon is carbon tetrachloride.

6. A process according to claim 1 wherein $R^2$, $R^3$ and $R^4$ represent hydrogen or a methyl group and $R^1$ and $R^5$ represent hydrogen atoms.

7. A process according to claims 1, 6, 2 or 3 wherein the halogenated hydrocarbon is a chlorinated hydrocarbon containing one to four carbon atoms.

8. A process according to claims 1, 6, 2 or 3 wherein the aromatic hydrocarbon is xylene.

* * * * *